United States Patent [19]

Lashier et al.

[11] Patent Number: 5,689,028
[45] Date of Patent: Nov. 18, 1997

[54] PROCESS TO REGULATE OLEFIN PRODUCTION BY CATALYST SYSTEM INHIBITION

[75] Inventors: Mark E. Lashier; Jeffrey W. Freeman; Ronald D. Knudsen, all of Bartlesville, Okla.

[73] Assignee: Phillips Petroleum Company, Bartlesville, Okla.

[21] Appl. No.: 573,655

[22] Filed: Dec. 18, 1995

Related U.S. Application Data

[63] Continuation of Ser. No. 199,861, Feb. 18, 1994, abandoned.

[51] Int. Cl.$^6$ ............................... C07C 2/24; B01J 31/00
[52] U.S. Cl. ........................ 585/512; 585/513; 585/523; 502/167
[58] Field of Search ........................... 585/512, 513, 585/523, 833, 836; 502/22, 27, 31, 167

[56] References Cited

U.S. PATENT DOCUMENTS

| | | | |
|---|---|---|---|
| 4,143,085 | 3/1979 | Funada et al. | 585/856 |
| 4,197,398 | 4/1980 | Floyd et al. | 528/488 |
| 4,395,356 | 7/1983 | Slaugh et al. | 528/487 |
| 4,409,414 | 10/1983 | Langer | 585/524 |
| 4,668,838 | 5/1987 | Briggs | 585/513 |
| 4,716,206 | 12/1987 | Fujita et al. | 526/139 |
| 5,034,209 | 7/1991 | Ajioka et al. | 423/502 |
| 5,096,548 | 3/1992 | Lonhoff et al. | 204/89 |
| 5,157,172 | 10/1992 | Wanzke et al. | 570/168 |
| 5,198,563 | 3/1993 | Reagen et al. | 556/57 |
| 5,288,823 | 2/1994 | Reagen et al. | |

OTHER PUBLICATIONS

Sax, N. Irving and Lewis, Sr., Richard J. Lewis; *Hawley's Condensed Chemical Dictionary* (1987) (11th Edition) pp. 48 and 910.

Grant, Roger and Grant, Claire; *Grant & Hackh's Chemical Dictionary* (5th Edition) pp. 28 and 29.

Briggs, John R.; *Journal Chem. Soc., Chem. Commun.* "The Selective Trimerization of Ethylene to Hex–1–ene", (1989), pp. 674–675.

*Primary Examiner*—Ponnathapura Achutamurthy
*Attorney, Agent, or Firm*—Lynda S. Jolly

[57] ABSTRACT

A process is provided to inhibit trimerization catalyst system activity which comprises the sequential steps of contacting a reactor effluent stream with alcohol; removing any desired olefin products; adding an aqueous base to the non-olefin portion; removing a precipitate; separating the aqueous and organic phases; and adding an acid to the aqueous phase.

21 Claims, No Drawings

PROCESS TO REGULATE OLEFIN PRODUCTION BY CATALYST SYSTEM INHIBITION

This application is a File Wrapper Continuation of application Ser. No. Ser. No. 08/199,861, filed Feb. 18, 1994, now abandoned.

BACKGROUND OF THE INVENTION

This invention relates to olefin preparation and catalyst recovery and recycle.

Olefins, primarily alpha-olefins, have many uses. In addition to uses as specific chemicals, alpha-olefins are used in polymerization processes either as a monomer or a comonomer to prepare polyolefins, or polymers. Unfortunately, during the production of olefins, a significant reaction by-product can be a polymeric material. Polymer production during the course of olefin preparation is detrimental to the process and reactor because polymer can build up on the interior walls or other portions of the reactor and inhibit heat transfer. Furthermore, any polymer produced needs to be separated from the olefin products stream, and/or a low molecular weight polymer can be formed causing a sticky, glue-like substance throughout the process and reactor.

SUMMARY OF THE INVENTION

Accordingly, it is an object of this invention to provide a process which will effectively deactivate, inhibit, and/or "kill" an olefin production catalyst.

It is a further object of this invention to provide a process which will halt polymer production in an olefin production process.

It is another object of this invention to provide a process which can remove an olefin production catalyst from the product stream.

It is yet another object of this invention to recover catalyst by-products for recycle, and/or recovery.

In accordance with this invention, a process is provided which can deactivate a catalyst useful for the production of olefins which comprises the sequential steps of contacting a reactor effluent stream with alcohol; removing and recovering any desired olefin product(s); adding an aqueous base to the reactor stream effluent, i.e., the non-olefin containing portion; removing a solid product, i.e., precipitate, from the reactor stream effluent; separating organic and aqueous phases; and adding an acid to the aqueous phase and recovering a precipitate.

DETAILED DESCRIPTION OF THE INVENTION

Catalyst Systems

Catalyst systems useful in accordance with this invention comprise a chromium source, a pyrrole-containing compound and a metal alkyl, all of which have been contacted and/or reacted in the presence of an unsaturated hydrocarbon. Optionally, these catalyst systems can be supported on an inorganic oxide support. These catalyst systems are especially useful for the dimerization and trimerization of olefins, such as, for example, ethylene to 1-hexene.

The chromium source can be one or more organic or inorganic compounds, wherein the chromium oxidation state is from 0 to 6. Generally, the chromium source will have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, can be made of mixed aliphatic, aromatic, and/or cycloaliphatic groups. Exemplary inorganic radicals include, but are not limited to halides, sulfates, and/or oxides.

Preferably, the chromium source is a chromium(II)- and/or chromium(III)-containing compound which can yield a catalyst system with improved oligomerization and/or trimerization activity. Most preferably, the chromium source is a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/or chromium dionates. Specific exemplary chromium(III) compounds include, but are not limited to, chromium(III) 2,2,6,6,-tetramethylheptanedionate [$Cr(TMHD)_3$], chromium(III) 2-ethylhexanoate [$Cr(EH)_3$ or chromium(III) tris(2-ethylhexanoate)] chromium(III) naphthenate [$Cr(Np)_3$], chromium(III) chloride, chromic bromide, chromic fluoride, chromium(III) acetylacetonate, chromium(III) acetate, chromium(III) butyrate, chromium(III) neopentanoate, chromium(III) laurate, chromium(III) stearate, chromium(III) pyrrolides and/or chromium(III) oxalate.

Specific exemplary chromium(II) compounds include, but are not limited to, chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate and/or chromium(II) pyrrolides.

The pyrrole-containing compound can be any pyrrole-containing compound that will react with a chromium source to form a chromium pyrrolide complex. As used in this disclosure, the term "pyrrole-containing compound" refers to hydrogen pyrrolide, i.e., pyrrole ($C_4H_5N$), derivatives of hydrogen pyrrolide, substituted pyrrolides, as well as metal pyrrolide complexes. A "pyrrolide" is defined as a compound comprising a 5-membered, nitrogen-containing heterocycle, such as for example, pyrrole, derivatives of pyrrole, and mixtures thereof. Broadly, the pyrrole-containing compound can be pyrrole and/or any heteroleptic or homoleptic metal complex or salt, containing a pyrrolide radical, or ligand. The pyrrole-containing compound can be either affirmatively added to the reaction, or generated in-situ.

Generally, the pyrrole-containing compound will have from about 4 to about 20 carbon atoms per molecule. Exemplary pyrrolides are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, and mixtures thereof. When the pyrrole-containing compound contains chromium, the resultant chromium compound can be called a chromium pyrrolide.

The most preferred pyrrole-containing compounds used in a trimerization catalyst system are selected from the group consisting of hydrogen pyrrolide, i.e., pyrrole ($C_4H_5N$), 2,5-dimethylpyrrole and/or chromium pyrrolides because of enhanced trimerization activity. Optionally, for ease of use, a chromium pyrrolide can provide both the chromium source and the pyrrole-containing compound. As used in this disclosure, when a chromium pyrrolide is used to form a catalyst system, a chromium pyrrolide is considered to provide both the chromium source and the pyrrole-containing compound. While all pyrrole-containing compounds can produce catalyst systems with high activity and productivity, use of pyrrole and/or 2,5-dimethylpyrrole can produce a catalyst system with enhanced activity and selectivity to a desired product.

The metal alkyl can be any heteroleptic or homoleptic metal alkyl compound. One or more metal alkyls can be used. The alkyl ligand(s) on the metal can be aliphatic and/or aromatic. Preferably, the alkyl ligand(s) are any saturated or unsaturated aliphatic radical. The metal alkyl can have any number of carbon atoms. However, due to commercial availability and ease of use, the metal alkyl will usually comprise less than about 70 carbon atoms per metal alkyl molecule and preferably less than about 20 carbon atoms per molecule. Exemplary metal alkyls include, but are not limited to, alkylaluminum compounds, alkylboron compounds, alkylmagnesium compounds, alkylzinc compounds and/or alkyl lithium compounds. Exemplary metal alkyls include, but are not limited to, n-butyl lithium, s-butyllithium, t-butyllithium, diethylmagnesium, diethylzinc, triethylaluminum, trimethylaluminum, triisobutylalumium, and mixtures thereof.

Preferably, the metal alkyl is selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. The use of hydrolyzed metal alkyls can result is decreased olefin, i.e., liquids, production and increased polymer, i.e., solids, production.

Most preferably, the metal alkyl is a non-hydrolyzed alkylaluminum compound, expressed by the general formulae $AlR_3$, $AlR_2X$, $AlRX_2$, $AlR_2OR$, $AlRXOR$, and/or $Al_2R_3X_3$, wherein R is an alkyl group and X is a halogen atom. Exemplary compounds include, but are not limited to, triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, and mixtures thereof for best catalyst system activity and product selectivity. The most preferred alkylaluminum compound is triethylaluminum, for best results in catalyst system activity and product selectivity.

Usually, contacting and/or reacting of the chromium source, pyrrole-containing compound and a metal alkyl is done in an unsaturated hydrocarbon. The unsaturated hydrocarbon can be any aromatic or aliphatic hydrocarbon, in a gas, liquid or solid state. Preferably, to affect thorough contacting of the chromium source, pyrrole-containing compound, and metal alkyl, the unsaturated hydrocarbon will be in a liquid state. The unsaturated hydrocarbon can have any number of carbon atoms per molecule. Usually, the unsaturated hydrocarbon will comprise less than about 70 carbon atoms per molecule, and preferably, less than about 20 carbon atoms per molecule, due to commercial availability and ease of use. Exemplary unsaturated, aliphatic hydrocarbon compounds include, but are not limited to, ethylene, 1-hexene, 1,3-butadiene, and mixtures thereof. The most preferred unsaturated aliphatic hydrocarbon compound is 1-hexene, because of elimination of catalyst system preparation steps and 1-hexene can be a reaction product. Exemplary unsaturated aromatic hydrocarbons include, but are not limited to, toluene, benzene, xylene, mesitylene, hexamethylbenzene, and mixtures thereof. Unsaturated, aromatic hydrocarbons are preferred in order to improve catalyst system stability, as well as produce a highly active and selective catalyst system. The most preferred unsaturated aromatic hydrocarbon is toluene.

It should be recognized, however, that the reaction mixture comprising a chromium source, pyrrole-containing compound, metal alkyl and unsaturated hydrocarbon can contain additional components which do not adversely affect and can enhance the resultant catalyst system, such as, for example, halides.

Reactants

Trimerization, as used in this disclosure, is defined as the combination of any two, three, or more olefins, wherein the number of olefin, i.e., carbon-carbon double bonds is reduced by two. Reactants applicable for use in the trimerization process of this invention are olefinic compounds which can a) self-react, i.e., trimerize, to give useful products such as, for example, the self reaction of ethylene can give 1-hexene and the self-reaction of 1,3-butadiene can give 1,5-cyclooctadiene; and/or b) olefinic compounds which can react with other olefinic compounds, i.e., co-trimerize, to give useful products such as, for example, co-trimerization of ethylene plus hexene can give 1-decene and/or 1-tetradecene, co-trimerization of ethylene and 1-butene can give 1-octene, co-trimerization of 1-decene and ethylene can give 1-tetradecene and/or 1-docosene. For example, the number of olefin bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term "trimerization" is intended to include dimerization of diolefins, as well as "co-trimerization", both as defined above.

Suitable trimerizable olefin compounds are those compounds having from about 2 to about 30 carbon atoms per molecule and having at least one olefinic double bond. Exemplary mono-1-olefin compounds include, but are not limited to acyclic and cyclic olefins such as, for example, ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and mixtures of any two or more thereof. Exemplary diolefin compounds include, but are not limited to, 1,3-butadiene, 1,4-pentadiene, and 1,5-hexadiene. If branched and/or cyclic olefins are used as reactants, while not wishing to be bound by theory, it is believed that steric hindrance could hinder the trimerization process. Therefore, the branched and/or cyclic portion(s) of the olefin preferably should be distant from the carbon-carbon double bond.

Catalyst systems produced in accordance with this invention preferably are employed as trimerization catalyst systems.

Reaction Conditions

The reaction products, i.e., olefin trimers as defined in this specification, can be prepared from the catalyst systems of this invention by solution reaction, slurry reaction, and/or gas phase reaction techniques using conventional equipment and contacting processes. Contacting of the monomer or monomers with a catalyst system can be effected by any manner known in the art. One convenient method is to suspend the catalyst system in an organic medium and to agitate the mixture to maintain the catalyst system in solution throughout the trimerization process. Other known contacting methods can also be employed.

Reaction temperatures and pressures can be any temperature and pressure which can trimerize the olefin reactants. Generally, reaction temperatures are within a range of about 0° to about 250° C. Preferably, reaction temperatures within a range of about 60° to about 200° C. and most preferably, within a range of 80° to 150° C. are employed. Generally, reaction pressures are within a range of about atmospheric to about 2500 psig. Preferably, reaction pressures within a range of about atmospheric to about 1000 psig and most preferably, within a range of 300 to 700 psig are employed.

Too low of a reaction temperature can produce too much undesirable insoluble product, such as, for example, polymer, and too high of a temperature can cause decomposition of the catalyst system and reaction products. Too low of a reaction pressure can result in low catalyst system activity.

Optionally, hydrogen can be added to the reactor to accelerate the reaction and/or increase catalyst system activity.

Catalyst systems of this invention are particularly suitable for use in trimerization processes. The slurry process is generally carried out in an inert diluent (medium), such as a paraffin, cycloparaffin, or aromatic hydrocarbon. Exemplary reactor diluents include, but are not limited to, isobutane and cyclohexane. Isobutane can be used for enhanced compatibility with known olefin polymerization processes. However, a homogenous trimerization catalyst system is more soluble in cyclohexane. Therefore, a preferred diluent for a homogeneous catalyzed trimerization process is cyclohexane. When the reactant is predominately ethylene, a temperature in the range of about 0° to about 300° C. generally can be used. Preferably, when the reactant is predominately ethylene, a temperature in the range of about 60° to about 110° C. is employed.

Products

The olefinic products of this invention have established utility in a wide variety of applications, such as, for example, as monomers for use in the preparation of homopolymers, copolymers, and/or terpolymers.

The further understanding of the present invention and its advantages will be provided by reference to the following examples.

After the aforementioned catalyst system has been used to prepare one or more olefin product(s), and the olefin production, i.e., trimerization, process is deemed to be complete, the reactor effluent stream comprising olefin product(s), catalyst system, and some polymer and/or oligomer, is contacted with an alcohol. Any alcohol which is soluble in the reactor effluent stream can be used. Preferably, an alcohol is selected that has a boiling point, or molecular weight, such that the alcohol will not azeotrope with the olefin monomer product. In an exemplary process, wherein the catalyst system is used to trimerize ethylene to 1-hexene, an alcohol with six or more carbon atoms per molecule is preferred. Most preferably, an alcohol having six to twelve carbon atoms per molecule is used for best catalyst system deactivation. Such alcohols are easily removable from the 1-hexene olefin product. Exemplary alcohols include, but, are not limited, 1-hexanol, 2-hexanol, 3-hexanol, 2-ethyl-1-hexanol, 3-octanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, and mixtures thereof.

The amount of alcohol to be added to the reactor effluent stream is in an amount sufficient to deactivate, or "kill", the olefin production catalyst system and to inhibit, or halt, production of undesirable solids, i.e., polymer. However, if an insufficient amount alcohol is used, metals in the catalyst system, such as for example, chromium and/or aluminum, can precipitate and can have a negative effect on future effluent processing. Generally, the amount of alcohol added can be up to about 5 molar equivalents of alcohol per total moles of metal in the effluent stream. Preferably, the amount of alcohol added is about 1 to about 4 molar equivalents, and most preferably the amount of alcohol added is 2 to 3 molar equivalents of alcohol per total moles of metal in the reactor effluent stream.

After the catalyst has been deactivated, or "killed", olefin product(s), such as, for example, 1-hexene, can be removed. Any removal process can be used, although distillation is preferred for ease of use.

The waste product steam, which has had the desired olefin monomer product(s) removed, then can be contacted with an aqueous base. Organic bases are not preferred because organic bases can be too weak to precipitate desired metals, such as, for example, chromium and/or aluminum. Preferred aqueous inorganic bases are selected from the group consisting of sodium hydroxide and potassium hydroxide, due to ease of use, availability, as well as beneficial effects on future processing. The amount of aqueous inorganic base added can any amount sufficient to precipitate substantially all of the chromium and a minimal amount of aluminum. The most important aspect of this step is to remove chromium. Addition of too much aqueous inorganic base can redissolve chromium back into solution, while an insufficient amount of aqueous inorganic base cannot precipitate substantially all of the chromium. Generally, about up to about 4 molar equivalents of aqueous inorganic base per mole of chromium and aluminum is sufficient. Preferably, an amount within in a range of about 0.2 to about 3 molar equivalents, and most preferably an amount within a range of 1 to 2 molar equivalents of aqueous inorganic base per mole of chromium and aluminum is sufficient.

The chromium-containing solid precipitate then can be removed and disposed of properly.

Following removal of the chromium containing solid precipitate, the aqueous and organic layers, or portions, are separated. The organic layer can be disposed of properly.

A mineral acid than can be added to the aqueous phase, or layer. Exemplary mineral acids include, but are not limited to, sulfuric acid, phosphoric acid, and mixtures thereof. Sulfuric acid is most preferred because sulfuric acid is the least corrosive mineral acid and, when used in the presence of potassium hydroxide and contacted with aluminum, can crystallize as $KAl(SO_4)_2$, or $KAl(SO_4)_2 \cdot 12H_2O$ commonly known as alum. Alum is frequently used in bulk quantities at water treatment facilities. Any amount of a mineral acid can be added to the aqueous layer to remove substantially all of the remaining aluminum ions. Too much mineral acid can increase the pH and therefore, the corrosivity of the aqueous solution. An insufficient amount of mineral acid will not precipitate substantially all of the aluminum. Generally, up to about 5 molar equivalents of sulfuric acid per mole of aluminum are sufficient. Preferably, about 1 to about 4, and most preferably, about 1 to about 3 molar equivalents of sulfuric acid per mole of aluminum are used, for the reasons stated above.

Optionally, an additional step can be removal of any remaining pyrrole-containing compound from the aqueous phase prior to the addition of a mineral acid. The presence of a pyrrole-containing compound can cause discoloration of the alum from a white to a variety of colors. Any method useful for removing organic compounds can be used. Exemplary pyrrole-containing compound removal methods include, but are not limited to, contacting the aqueous layer and/or alum with activated carbon and/or the use of hydrogen peroxide.

Any reaction conditions which can affect the above-mentioned steps are useful. However, for ease of use, ambient temperatures and ambient pressures are preferred. Most preferably, an inert atmosphere can be used so that the organic phase, which can contain some pyrrole-containing compound, does not discolor.

EXAMPLES

Example 1

An exemplary catalyst system was prepared under an inert atmosphere (nitrogen) using chromium(III) 2-ethylhexanoate (21.3 mmol Cr), 2,5-dimethylpyrrole (63.8 mmol), ethylaluminum dichloride (85.1 mmol) and triethylaluminum (319 mmol) as follows: Chromium (III) 2-ethylhexanoate was dissolved in 100 mL anhydrous toluene and 2,5-dimethylpyrrole added to the resulting dark green solution. In a separate container, ethylaluminum dichloride and triethylaluminum were mixed together. Then, the aluminum alkyl solution was poured slowly into the chromium/pyrrole solution. The resulting dark yellow-brown solution was stirred for 5 minutes and then the solvent removed in vacuo. The remaining oily liquid was diluted to 150 mL with cyclohexane and allowed to set overnight, under nitrogen, at room temperature and pressure. The solution then was filtered to remove a black precipitate from the filtrate, which contained the catalyst system, and was diluted to a volume of 250 mL using cyclohexane.

The catalyst system solution was placed in a 1-liter flask equipped with a nitrogen inlet and a stir bar, under an inert nitrogen atmosphere. The flask then was cooled with an water/ice bath. The catalyst system was deactivated by slow addition of n-butyl alcohol (1090 mmol) from a syringe against a nitrogen purge. The deactivation is an exothermic reaction; gasses formed during the deactivation were vented with the nitrogen purge.

A solution of potassium hydroxide (540 mmol) in 200 mL water then was added to the deactivated catalyst system and the resulting mixture stirred for 15 minutes to facilitate the reaction. The solution was filtered to remove a green, chromium containing precipitate. The organic phase of the filtrate was separated from the aqueous phase and analyzed.

The aqueous phase was acidified using 770 mmol sulfuric acid in 150 mL of water. Acidification of the aqueous phase liberated a small amount of organic material that was separated and saved for analysis. The aqueous phase was heated with 2–3 mL 30% hydrogen peroxide to remove trace organics, concentrated to about 200 mL and filtered while hot. The filtrate was cooled in ice water and the alum crystals that formed were collected and dried. For the purposes of analysis, the supernatant from the alum crystallization was evaporated to dryness.

Products from the deactivation were analyzed by X-ray spectroscopy for Cr, Al and K. The results are listed below in Table 1, as Run 101.

The same procedure was used in Run 102, as was used in Run 101, except that the amount of reagents used were different. In Run 102, the catalyst system was prepared using chromium(III) 2-ethylhexanoate (3.85 mmol Cr), 2,5-dimethylpyrrole (3.85 mmol), ethylaluminum dichloride (7.7 mmol) and triethylaluminum (30.7 mmol). Catalyst system was diluted to 50 mL.

Deactivation was carried out using 130 mmol 2-ethyl-1-hexanol. Precipitation of the chromium required 71 mmol potassium hydroxide. Acidification required 145 mmol sulfuric acid. Results of metals analyses (plasma and/or X-ray) are given below in Table 1.

The same procedure was used in Run 103 as was used in Run 102 except that the catalyst system was used in a reactor, i.e., to produce a product before deactivation.

The reaction of the catalyst system with ethylene was carried out in a 1-liter autoclave reactor at 110° C. The catalyst system was diluted to about 450 mL in cyclohexane. Ethylene was fed to the reactor at a rate of 850 g/hr for 30 minutes. The pressure in the reactor was 475 psig at the end of 30 minutes. The reactor then was cooled to 55° C. and the used catalyst system collected under nitrogen in a 1-liter flask. Catalyst system deactivation was carried out as in Run 102. Results are given below in Table 1.

The same procedure was used for Run 104 as was used in Run 101 except that the amount of reagents used were different. In Run 104, the catalyst system was prepared using chromium(III) 2-ethylhexanoate (19.2 mmol Cr), 2,5-dimethylpyrrole (34.6 mmol), ethylaluminum dichloride (48.1 mmol) and triethylaluminum (154 mmol). Catalyst system was diluted to 250 mL.

Deactivation was carried out using 665 mmol 2-ethyl-1-hexanol. Precipitation of the chromium required 370 mmol potassium hydroxide. Acidification required 410 mmol sulfuric acid. Results of metals analyses (plasma and/or X-ray) are given below in Table 1.

TABLE 1

Results of Metals Analyses

| | Weight, g | Cr, ppm | Cr, wt % | Al, wt % | K, wt % |
|---|---|---|---|---|---|
| Run 101 | | | | | |
| Green precipitate | 25.5 | 28000 | 100 | 21.7 | 8.7 |
| Alum | 65.7 | * | 0 | 5.3 | 7.0 |
| Supernatant | 40.0 | * | 0 | 2.6 | 3.8 |
| Organic Residue | 2.9 | * | 0 | 0.7 | 67.9 |
| Run 102 | | | | | |
| Green precipitate | 1.4 | 60000 | 90.8 | 17 | 11.7 |
| Aqueous phase | 16.3 | 36.3 | 0.6 | NA | 13.3 |
| Organic Residue | 0.81+ | 3422 | 8.5 | NA | <.1 |
| Run 103 | | | | | |
| Green precipitate | 3.48 | 9000 | 84.8 | 19.9 | 2.9 |
| Aqueous phase | 12.4 | 400 | 13.5 | NA | 18.2 |
| Organic Residue | 0.41+ | 1675 | 1.6 | NA | <.1 |
| Run 104 | | | | | |
| Green precipitate | 14.8 | 31000 | 98.9 | 14.9 | 15.8 |
| Alum | 37.5 | <18 | 0.2 | NA | 8.0 |
| Supernatant | 16.3 | 117 | 0.4 | NA | 3.7 |
| Organic Residue | 8.7+ | 314 | 0.6 | NA | NA |

*Level below detection limit of 500 mg/Kg
NA Not Analyzed
+ Combined Organic Residue

Example 2

The same catalyst preparation procedure was followed in Runs 201–208 as in Example 1, except that the amount of reagents used was different. In Runs 201–208, catalyst system was prepared using chromium(III) 2-ethylhexanoate (2.93 mmol Cr), 2,5-dimethylpyrrole (11.7 mmol), ethyl aluminum dichloride (EADC) (14.6 mmol), and triethylaluminum (TEA) (44.0 mmol). Catalyst system was diluted to 250 ml with cyclohexane and treated as in Example 1.

Runs 201–208 were carried out in a continuous stirred tank reactor system which included feed systems for catalyst, reagent(s) and solvent(s); a 1-gallon magnetically stirred Autoclave reactor; a polymer filter; a gas chromatograph; and a product receiver. The polymer filter was a 1-liter autoclave cooled with ambient water via an internal coil. The filter volume was filled with stainless steel mesh filter material. For each Run, catalyst system solution was fed to the reactor at a rate of 30 ml/hr; ethylene was fed at a rate of about 1790 g/hr; solvent (cyclohexane) was fed at a rate of about 0.75 gal/hr; reactor temperature was 115° C.; and reactor pressure was 715 psia. Hydrogen was fed to the reactor at different rates for each Run. Catalyst deactivating/kill agent (1-butanol) was fed at varying points downstream of the reactor at a rate of 15 ml/hr. A slip stream of reactor effluent was sampled every hour for 6 hours to determine reactant conversion and product selectivity. Each Run achieved steady state conditions.

In addition to conversion and selectivity, the amount of polymer generated in each Run was monitored. Polymer was differentiated as that which passed into the filter and that which remained in the reactor. The weight of each polymer fraction collected was normalized to the amount of 1-hexene produced in that particular Run and is given as grams polymer produced per gram 1-hexene produced. Data are presented below in Table 2.

wherein said catalyst system comprises a chromium source, a pyrrole-containing compound and an alkylaluminum compound;

b) separating the product stream of (a) by removing and recovering at least one olefin trimerization product to form a product portion and a waste portion;

c) adding an aqueous, inorganic base to the waste portion of (b), to form an aqueous phase which comprises the inorganic base; an organic phase which comprises olefin product(s), polymer(s) and/or oligomer(s); and a precipitate which comprises chromium;

d) removing the precipitate from the aqueous phase and organic phase;

e) separating the aqueous phase and organic phase; and f) adding a mineral acid selected from the group consisting of sulfuric acid, phosphoric acid and mixtures thereof to the aqueous phase to remove substantially all of the aluminum.

2. A process according to claim 1 wherein said reactor effluent stream comprises olefin product(s); an olefin trimerization catalyst system; an organic diluent; one or more mono-olefins; and polymer.

3. A process according to claim 2 wherein said alcohol has a boiling point different from the olefin product in the reactor influent stream.

4. A process according to claim 3 wherein said alcohol has 6 or more carbon atoms per molecule.

5. A process according to claim 1 wherein said aqueous base is in an aqueous inorganic base selected from the group consisting of sodium hydroxide, potassium hydroxide, and mixtures thereof.

6. A process according to claim 5 wherein said aqueous inorganic base is potassium hydroxide.

TABLE 2

Results of Polymer Mitigation

| | | | | | Polymer (g/g 1-hexene) | |
|---|---|---|---|---|---|---|
| Run | $H_2$,[a] slph | Kill Agent Addition Point | Ethylene Conversion (%) | 1-Hexene Selectivity (%) | Total[b] ($\times 10^{-4}$) | Reactor ($\times 10^{-6}$) |
| 201 | none | filter vessel | 81 | 91 | 3.5 | 1.7 |
| 202 | 2.1 | filter vessel | 84 | 89 | 2.3 | 1.0 |
| 203 | 6.1 | filter vessel | 77 | 93 | 3.2 | 0 |
| 204 | 18.2 | filter vessel | 79 | 91 | 3.1 | 1.1 |
| 205 | none | reactor outlet | 75 | 93 | 0.6 | 8.3 |
| 206 | 2.0 | reactor outlet | 68 | 90 | 0.7 | 1.2 |
| 207 | 6.1 | reactor outlet | 72 | 90 | 1.1 | 1.1 |
| 208 | 18.2 | reactor outlet | 74 | 93 | 0.3 | 0 |

[a]slph = standard liters per hour
[b]Total amount in filter and reactor.

While this invention has been described in detail for the purpose of illustration, it is not to be construed as limited thereby but is intended to cover all changes and modifications within the spirit and scope thereof.

That which is claimed is:

1. A process to inhibit an olefin trimerization catalyst system activity and to recover trimerization products and trimerization catalyst system components comprising the sequential steps of:

a) forming a product stream by contacting an olefin trimerization reactor effluent stream which comprises olefin product(s), catalyst system, polymer(s) and/or oligomer(s) with an alcohol that is soluble in any portion of the reactor effluent stream;

7. A process according to claim 1 wherein said mineral acid is sulfuric acid.

8. A process according to claim 1 carried out under conditions of ambient temperature and pressure.

9. A process according to claim 1 wherein said alcohol is added in an amount of up to 5 molar equivalents of alcohol per the sum of moles of chromium and moles of aluminum of the alkylaluminum compound.

10. A process according to claim 1 wherein said aqueous, inorganic base is added in an amount of up to 5 molar equivalents of base per the sum of moles of chromium and moles of aluminum of the alkylaluminum compound.

11. A process according to claim 1 wherein said mineral acid is added in an amount of up to about 5 molar equivalents of acid per mole of aluminum of the alkyaluminum compound.

12. A process to inhibit an olefin trimerization catalyst system activity and to recover trimerization products and trimerization catalyst system components comprising the sequential steps of:

a) forming a product stream by contacting an olefin trimerization reactor effluent stream which comprises olefin product(s), catalyst system, polymer(s) and/or oligomer(s) with an alcohol that is soluble in any portion of the reactor effluent stream and has from six to twelve carbon atoms per molecule;

wherein said catalyst system comprises a chromium source, a pyrrole-containing compound and an alkylaluminum compound;

b) separating the product stream of (a) by removing and recovering at least one olefin trimerization product to form a product portion and a waste portion;

c) adding an aqueous inorganic base selected from the group consisting of sodium hydroxide, potassium hydroxide, and mixtures thereof to the waste portion of (b), to form an aqueous phase which comprises the inorganic base; an organic phase which comprises olefin product(s), polymer(s) and/or oligomer(s); and a precipitate which comprises chromium;

d) removing the precipitate from the aqueous phase and organic phase;

e) separating the aqueous phase and organic phase; and f) adding a mineral acid selected from the group consisting of sulfuric acid, phosphoric acid and mixtures thereof to the aqueous phase to remove substantially all of the aluminum.

13. A process according to claim 12 wherein said reactor effluent stream comprises olefin product(s): an olefin trimerization catalyst system; an organic diluent; one or more mono-olefins; and polymer.

14. A process according to claim 12 wherein said aqueous inorganic base is potassium hydroxide.

15. A process according to claim 12 wherein said mineral acid is sulfuric acid.

16. A process according to claim 12 carried out under conditions of ambient temperature and pressure.

17. A process according to claim 12 wherein said alcohol is added in an amount of up to 5 molar equivalents of alcohol per the sum of moles of chromium and moles of aluminum of the alkylaluminum compound.

18. A process according to claim 12 wherein said aqueous, inorganic base is added in an amount of up to 5 molar equivalents of base per the sum of moles of chromium and moles of aluminum of the alkylaluminum compound.

19. A process according to claim 12 wherein said mineral acid is added in an amount of up to about 5 molar equivalents of acid per mole of aluminum of the alkylaluminum compound.

20. A process according to claim 1 wherein said alkylaluminum compound is a trialkylaluminum compound.

21. A process according to claim 12 wherein said alkylaluminum compound is a trialkylaluminum compound.

* * * * *